US 6,815,949 B2

(12) United States Patent
Kandori et al.

(10) Patent No.: US 6,815,949 B2
(45) Date of Patent: Nov. 9, 2004

(54) APPARATUS FOR MEASURING A MAGNETIC FIELD

(75) Inventors: Akihiko Kandori, Kokubunji (JP); Tsuyoshi Miyashita, Fuchu (JP); Keiji Tsukada, Kashiwa (JP); Koichi Yokosawa, Kodaira (JP); Daisuke Suzuki, Kodaira (JP); Akira Tsukamoto, Toda (JP)

(73) Assignee: Hitachi, Ltd., Tokyo (JP)

( * ) Notice: Subject to any disclaimer, the term of this patent is extended or adjusted under 35 U.S.C. 154(b) by 151 days.

(21) Appl. No.: 10/162,748

(22) Filed: Jun. 6, 2002

(65) Prior Publication Data

US 2003/0016010 A1 Jan. 23, 2003

(30) Foreign Application Priority Data

Jul. 19, 2001 (JP) ........................................ 2001-218951

(51) Int. Cl.[7] .......................... G01R 33/035; A61B 5/05
(52) U.S. Cl. ........................ 324/248; 600/409; 327/527
(58) Field of Search ................................ 600/407–408, 600/409, 421–422; 327/366–367, 370, 527–528; 505/846; 324/244, 248, 228, 235, 301, 318, 322

(56) References Cited

U.S. PATENT DOCUMENTS

| 5,045,788 A | * | 9/1991 | Hayashi et al. ............. 324/248 |
| 5,049,818 A | * | 9/1991 | Dossel et al. ............... 324/248 |
| 5,093,618 A | * | 3/1992 | Goto et al. ................. 324/248 |
| 5,254,950 A | * | 10/1993 | Fan et al. ................... 324/322 |
| 5,343,707 A | * | 9/1994 | Sata ............................... 62/6 |
| 5,414,356 A | * | 5/1995 | Yoshimura et al. ......... 324/239 |
| 5,421,345 A | * | 6/1995 | Lekholm et al. ............ 600/547 |
| 5,537,037 A | * | 7/1996 | Otaka et al. ................ 324/240 |
| 6,420,868 B1 | * | 7/2002 | Ganther et al. ............. 324/248 |

FOREIGN PATENT DOCUMENTS

| JP | 06-225860 | 12/1993 |
| JP | 6-324021 | 3/1994 |

OTHER PUBLICATIONS

W.G. Kubicek, Ph.D., J.N. Karnegis, M.D., R.P. Patterson, M.S.E.E., D. A. Witsoe, M.S.E.E. and R.H. Mattson, Ph.D., "Development and Evaluation of an Impedance Cardiac Output System", Aerospace Medicine, Dec. 1966, pp. 1208–1212.

David G. Newman and Robin Callister, "The Non–Invasive assessment of Stroke Volume and Cardiac Output by Impedance Cardiograpy: A Review", Aviation, Space and Environment Medicine, vol. 70, No. 8, Aug. 1999, pp. 780–789.

Akihiko Kandori, Tsuyoshi Miyashita, Daisuke Suzuki, Koichi Yokosawa and Keiji Tsukada, "Impedance Magnetocardiogram", Phys. Med. Biol 46 (2001) pp. N45–N48.

(List continued on next page.)

Primary Examiner—Jay Patidar
Assistant Examiner—Darrell Kinder
(74) Attorney, Agent, or Firm—Reed Smith LLP; Stanley P. Fisher, Esq.; Juan Carlos A. Marquez, Esq.

(57) ABSTRACT

An apparatus can detect a magnetic field with a high sensitivity using an ordinary-temperature pickup coil even when the pickup coil is arranged outside a cryostat. Specifically, the apparatus for measuring a magnetic field includes a pickup coil for detecting an external magnetic field, a SQUID electrically or magnetically connected to the pickup coil, a cryostat for holding the SQUID at low temperatures, and a driving device for driving the SQUID. The pickup coil is made of a normal-conducting material and is placed at an ordinary temperature outside the cryostat. By arranging outside the cryostat, the pickup coil can be brought close to a subject and can thereby detect a weak magnetic field in the subject with a high sensitivity.

7 Claims, 15 Drawing Sheets

OTHER PUBLICATIONS

S. Kumar, R. Matthews, S.G. Haupt, D.K. Lathrop, M. Takigawa, J.R. Rozen, S.L. Brown and R.H. Koch, "Nuclrar Magnetic Resonance Using a High Temperature Superconducting Quantum Interference Device", Appl. Phys. Lett 70(8), Feb. 1997, pp. 1037–1039.

Martin Wurm, Jean–Pascal Brison, Jacques Flouquet, "Longitudinal Detection of Pusled Low–Frequency, Low–Temperature Nuclear Magnetic Resonance Using a dc SQUID", 1998 American Institute of Physics, Review of Scientific Instruments, vol. 69, No. 3, pp. 1456–1462.

* cited by examiner

APPARATUS FOR MEASURING A MAGNETIC FIELD

BACKGROUND OF THE INVENTION

1. Field of the Invention

The present invention relates to a magnetometer for measuring a weak magnetic field using a superconducting quantum interference device (hereinafter briefly referred to as SQUID). Specifically, it relates to an improved configuration of a magnetometer in which a high frequency current is fed to a living body, and the resulting change in magnetic field or a nuclear magnetic resonance signal is detected by a pickup coil magnetically or electrically connected to the SQUID. More specifically, it relates of a magnetometer including a normal conducting member as the pickup coil which is arranged outside a cryostat.

2. Description of the Related Arts

In a conventional apparatus for measuring a magnetic field, a pickup coil made of a superconducting member is used, and a SQUID and the pickup coil are both cooled to a superconducting state to thereby detect magnetic field changes with activities of neurons in brain cells (magnetoencephalography) or magnetic field changes with action currents of cardiac muscle cells (magnetocardiography). In this configuration, the pickup coil is inevitably arranged distant from an inspected subject.

Impedance cardiography has been developed in which a high frequency current is fed to a living body, and an electric potential varying with changes in blood volume flowing in the living body is measured in order to monitor changes in electric potential with mechanical motions such as blood flow or the systole and diastole of the heart [Aerospace Medicine; Vol. 37 (1966), pp. 1208–1212 (Reference 1) and Aviation, Space, and Environmental Medicine; Vol. 70, No. 8 (1999), pp. 780–789 (Reference 2)].

In another process, a high frequency current is applied to a living body to thereby measure a magnetic field [Phys. Med. Biol.; Vol. 46, (2001), pp. N45–N48 (Reference 3)]. This process uses a pickup coil placed inside a cryostat.

Japanese Patent Laid-Open No. 6-225860 (1994) (Reference 4) mentions an apparatus for measuring the spatial distribution of electrical impedance as an industrial field of the invention. In the apparatus, a source of electrical current is electrically connected to at least two feed electrodes which impress a feed current from the source in an examination region of a subject to form a current distribution corresponding to electrical impedance distribution and positions of the electrodes. The resulting magnetic field is measured at points outside the examination region, and an equivalent current density distribution is reconstructed within the examination region from the measured values of the magnetic field. The equivalent current density distribution at the measuring points is that which would be generated by a theoretical magnetic field which best coincides with the measured magnetic field caused by the distribution of the current. The invention described in this reference is directed to provide an apparatus for identifying the spatial distribution of electrical impedance in a subject which has a high sensitivity for the magnetic fields generated by the distribution of current in the examination region.

Alternatively, SQUIDs are used to detect a magnetic resonance signal with a high sensitivity [Appl. Phys. Lett.; Vol. 70, No. 8 (1997), pp. 1037–1039 (Reference 5) and Rev. Sci. Instrum.; Vol. 69, No. 3 (1998), pp. 1456–1462 (Reference 6)]. In such an apparatus using SQUIDs, the magnetic resonance signal is detected by a process in which a pickup coil is placed inside a cryostat as in conventional apparatus for measuring a magnetic field in a living body, or by a process in which a sample is placed in the cryostat, and the magnetic resonance signal in the sample is detected at cryogenic temperatures. According to the former process, the pickup coil cannot be sufficiently brought close to the inspected subject and SQUID magnetometer can not be operated because it should be placed in a static magnetic field. According to the latter process, the sample must be cooled to cryogenic temperatures, and the magnetic resonance signal cannot be detected in samples at an ordinary temperature.

Conventional impedance cardiography based on measurement of electric potential requires a large number of electrodes to identify the state of local blood and is not suitable as a general measuring method. A technique has therefore been developed for real-time and non-touch monitoring of a change in magnetic field with mechanical motion such as the blood flow or the systole and diastole of the heart (Reference 3). Such a change in magnetic field with mechanical motion such as the blood flow or the systole and diastole of the heart can be detected by using the conventional superconducting pickup coil placed inside the cryostat. However, according to this technique, the pickup coil cannot sufficiently be brought close to the inspected subject.

The technique described in Reference 4 can detect the distribution in electric impedance generated by the current fed from the feed electrode at a certain time but cannot detect, in real-time, a change in electric impedance with time.

SUMMARY OF THE INVENTION

Accordingly, an object of the present invention is to detect a change in magnetic field with a high sensitivity outside a cryostat using a SQUID magnetometer including a pickup coil made of a normal conducting material, which change in magnetic field is induced by mechanical motions such as a blood flow in an organ of a living body.

Another object of the present invention is to provide a SQUID magnetometer using an ordinary-temperature coil which can detect magnetic resonance signals with a high sensitivity even in a low magnetic field and can be brought in intimate contact with an inspected subject at an ordinary temperature.

To achieve the above objects, the present invention provides, in one aspect, an apparatus for measuring a magnetic field (a SQUID magnetometer). The apparatus includes a device for feeding a current to a living body; a pickup coil for detecting a magnetic field induced in the living body by action of the device for feeding a current; a superconducting quantum interference device; and a device for connecting the pickup coil to the superconducting quantum interference device. In the apparatus, the pickup coil is made of a normal conducting member.

In another aspect, the present invention provides an apparatus for measuring a magnetic field. This apparatus includes a device for feeding a current to a subject; a pickup coil for detecting a magnetic field in the subject; a superconducting quantum interference device; a cryostat for holding the superconducting quantum interference device; and a device for connecting the pickup coil to the superconducting quantum interference device. In the apparatus, the pickup coil is made of a normal conducting member and is arranged outside the cryostat.

In addition and advantageously, the present invention provides an apparatus for examination. This apparatus includes a device for applying an alternating current to an inspected subject; a detecting probe for detecting a magnetic field generated from the inspected subject; a superconducting quantum interference device connected to the detecting probe; a cryostat for holding the superconducting quantum interference device; and a detector for extracting a magnetic field with a desired frequency component from the detecting probe by using the alternating current applied to the inspected subject as a reference signal.

In the apparatus for measuring a magnetic field (SQUID magnetometer) of the present invention, a preferred configuration is as follows: Specifically, at least one pickup coil for measuring a magnetic field made of a normal conducting material is arranged outside the cryostat, and at least one SQUID electrically or magnetically connected to the pickup coil is arranged inside the cryostat. A cryogenic cooling medium is charged into the cryostat to thereby hold the SQUID in a superconducting state. At least two electrodes are placed in at least two positions, such as the head and leg, of a subject or at least two positions of a metal conductor. The apparatus includes a driving circuit for driving the SQUID and an oscillator for feeding a high frequency current to the electrodes. The output terminal of the driving circuit is connected to a high-pass filter circuit, a phase-shift detector, a band-pass filter circuit, and an amplifier. The apparatus further includes a device for feeding output signals (hereinafter, the output signal from the amplifier obtained by feeding the high frequency current to the subject is referred to as "impedance magnetocardiogram signal") from the amplifier to a computer to thereby collect data and for displaying and calculating the collected data. It further includes a coil for applying a compensation magnetic field with an inverse phase in the vicinity of the pickup coil, and a device for optimizing a magnetizing current fed to the compensation coil with an inverse phase based on the current data obtained from a differential amplifier for controlling the high frequency current flowing through the subject or the metal conductor.

DESCRIPTION OF THE PREFERRED EMBODIMENTS

The present invention will be illustrated in further detail with reference to several preferred embodiments below and attached drawings.

First Embodiment

Figure 1:
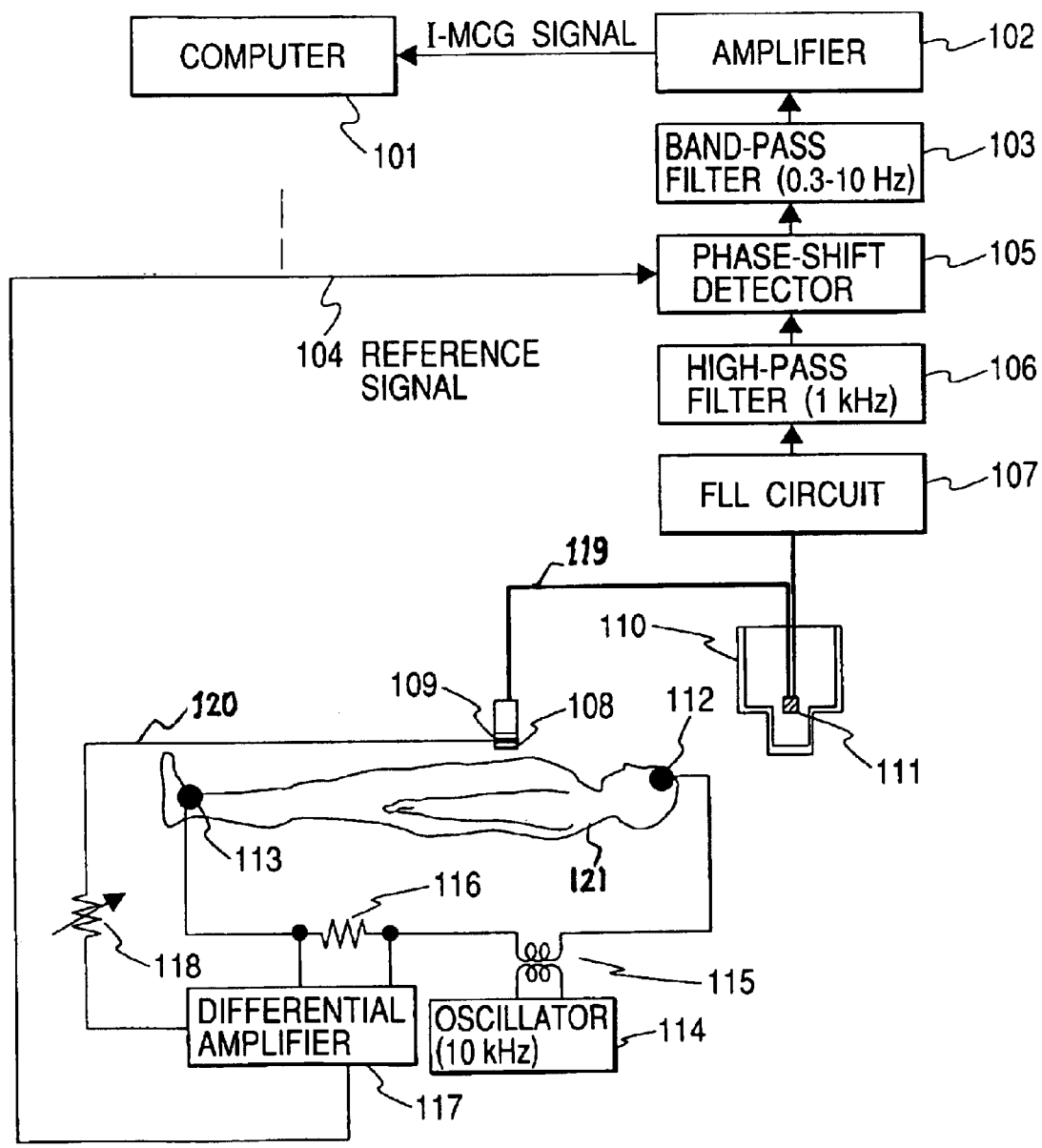
FIG. 1 is a schematic diagram of an apparatus for measuring a magnetic field as a first embodiment of the present invention.

FIG. 1 is a schematic diagram of an apparatus for measuring a magnetic field as the first embodiment of the present invention. A SQUID 111 is arranged in a cryostat 110 and is in a superconducting state by liquid helium stored in the cryostat 110. The SQUID 111 used in the present embodiment comprises a SQUID ring made of a member such as niobium, an input coil arranged on the SQUID ring, and a feedback coil arranged outside the input coil. These components are patterned on one chip. The input coil is electrically connected to a lead line part 119 and is thereby electrically connected to a pickup coil 108 via the lead line part 119. The SQUID 111 is connected to an FLL (flux locked loop) circuit 107 arranged outside the cryostat 110 to operate as a magnetometer. The output of the FLL circuit 107 is fed through a high-pass filter 106 having a cutoff frequency of 1 kHz to thereby remove low frequency noise. The output of the high-pass filter 106 is transferred to a phase-shift detector 105. The phase-shift detector 105 detects a phase shift using the frequency of an alternating current (a current of 10 kHz in this embodiment) applied to a subject 121 as a reference signal 104. In the present embodiment, the subject is a living subject. The reference signal 104 is generated by an oscillator 114. A signal generator which can vary its oscillating frequency, such as a function generator, is preferably used herein to control the reference signal at a desired level.

The signal passed through the phase-shift detector 105 then passes through a band-pass filter 103 and an amplifier 102 and is converted into digital data by a computer 101.

Figure 6:
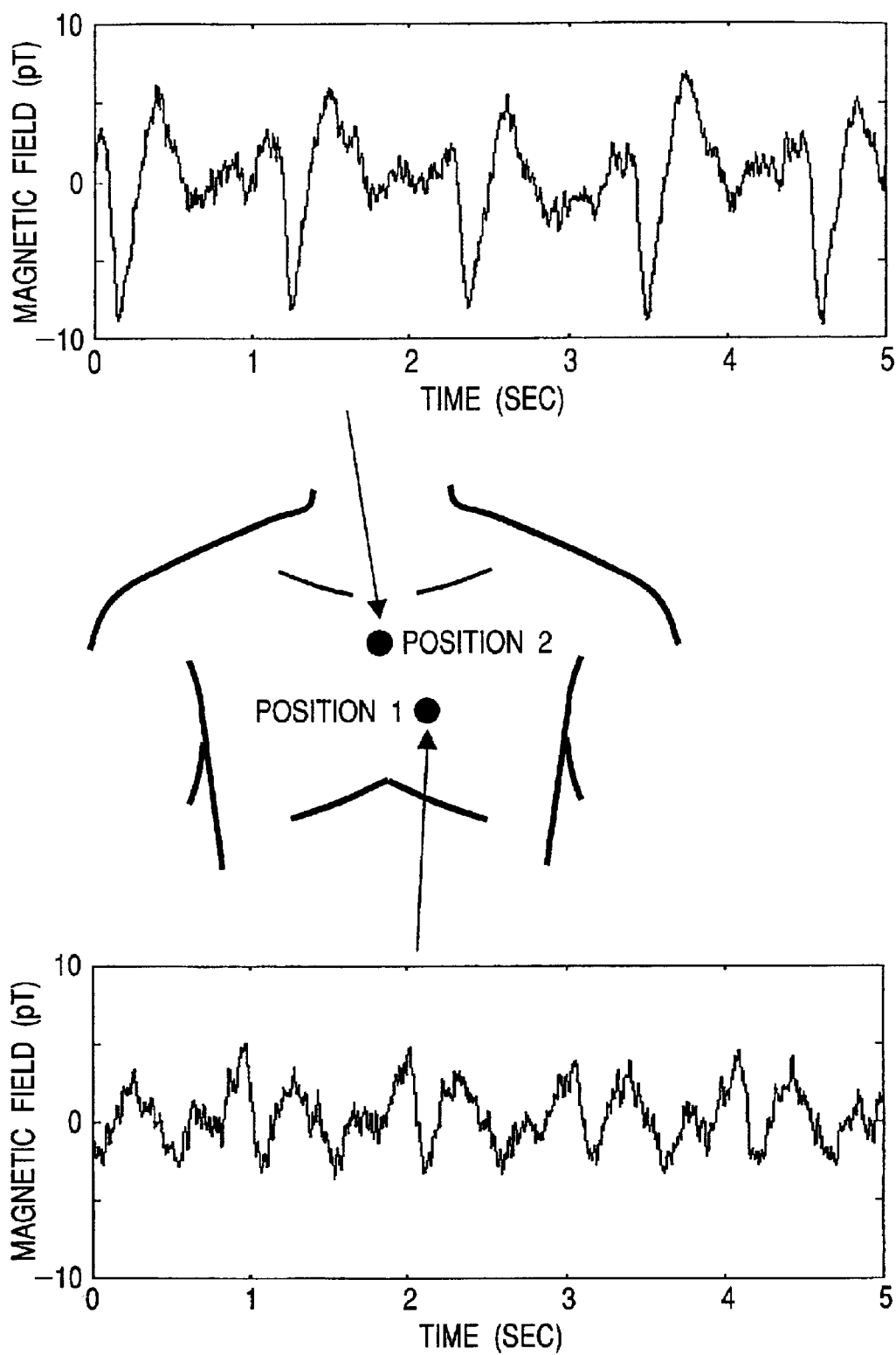
FIG. 6 is a waveform chart showing real-time waveforms as actual measurements of impedance magnetocardiograms in the apparatus of the first embodiment.
Figure 7A:
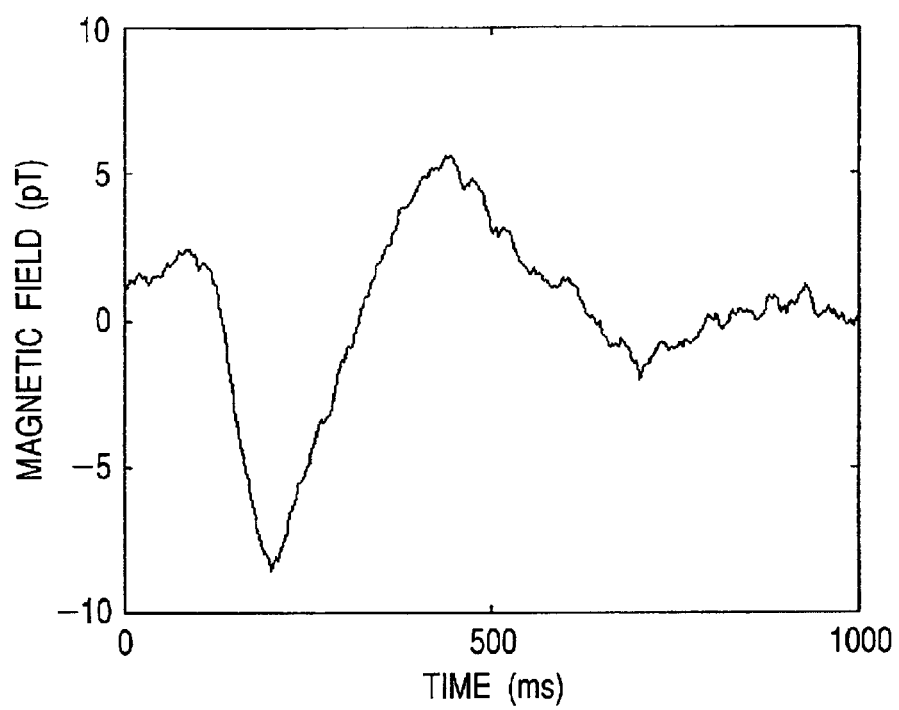
FIGS. 7(a) and 7(b) are waveform charts showing waveforms after 10-time averaging of the impedance magnetocardiograms shown in FIG. 6.
Figure 7B:
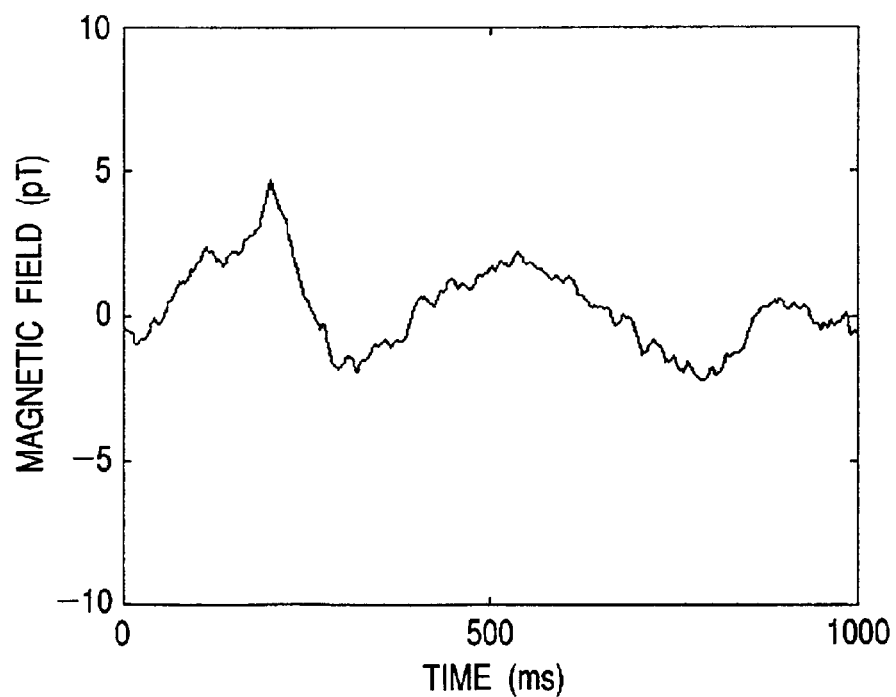

The computer 101 processes the digital data, for example, to display waveforms or to analyze waveforms as shown in FIG. 6 or FIGS. 7(a) and 7(b).

The cryostat 110 used in the present embodiment is not specifically limited to one storing a cooling medium such as liquid helium or liquid nitrogen and also includes one in which a cryocooler is connected to the cryostat 110. In the configuration of the present embodiment, low-frequency magnetic field noise is as low as to be trivial, and materials for the constitutional member of the cryostat are not limited to non-magnetic materials such as GFRPs (glass fiber reinforced plastics) and also include metal materials such as stainless steel. By using a cryostat made of stainless steel, vacuum maintenance and other maintenance of the cryostat can be simplified to thereby reduce evaporation of the cooling medium, and the cryostat can easily be ganged to the cryocooler.

An alternative voltage generated by the oscillator 114 is transferred via a transformer 115 to thereby apply an alternating current via carbon electrodes 112 and 113 to the subject 121. The transformer 115 is provided to avoid shock hazards of the subject. In order to monitor the frequency of the applied current, a potential between the both ends of a resistance 116 is amplified by a differential amplifier 117 and is detected. The output of the differential amplifier 117 branches into the reference signal 104 of the phase-shift detector 105 and into a lead line part 120. The lead line part 120 serves to generate a compensation magnetic field with an inverse phase to feed to the compensation coil with an inverse phase 109. By feeding a current to compensation coil with an inverse phase 109, which current has an inverse phase to that of a magnetic field detected by the pickup coil 108, the compensation magnetic field with an inverse phase can cancel a large magnetic field detected by the pickup coil 108. A variable resistance 118 controls the amount of current fed to the compensation coil with an inverse phase 109. Alternatively, an amplifier and a gain controller of the amplifier may control the amount of current.

Even in an apparatus for measuring a magnetic field in which the pickup coil is arranged inside the cryostat 111, the compensation coil with an inverse phase 109 can be arranged outside the cryostat 111 to thereby ensure the compensation magnetic field with an inverse phase to cancel a large magnetic field input into the pickup coil.

Figure 2:
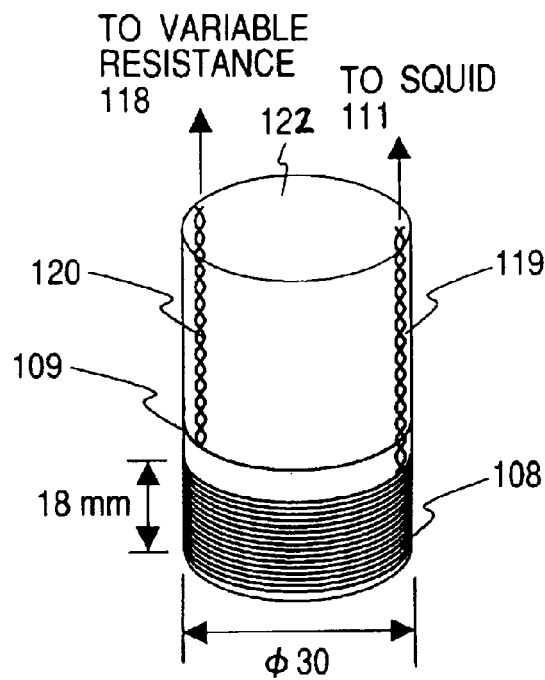
FIG. 2 is a perspective view illustrating a configuration of the pickup coil part of the apparatus of the first embodiment.

FIG. 2 illustrates the configuration of the magnetic field pickup part of the apparatus. The pickup coil 108 and the compensation coil with an inverse phase 109 are placed around a bobbin 122 made of poly(vinyl chloride) and having a diameter of 30 mm. The pickup coil 108 and the compensation coil with an inverse phase 109 are made of an enamel-coated copper wire (a normal conducting wire). The pickup coil 108 comprises two layers of 75 turns of the copper wire, a total of 150 turns, to thereby have an inductance of 0.7 mH. The lead line part 119 is twisted and is arranged in a direction identical to the direction of the detected magnetic field and opposite to that of the pickup coil 108. Likewise, the lead line part 120 of the compensation coil with an inverse phase 109 is twisted and is arranged in a direction identical to the direction of the detected magnetic field and opposite to that of the pickup coil 108. To avoid high frequency interference, it is preferred that the lead line parts 119 and 120 are made of a cable carrying a shielding means against external electromagnetic waves, such as a shielding wire made of aluminium, as an envelope and the shielding wire is grounded with the ground of the FLL circuit. When the electromagnetic noise is significant, the pickup coil is preferably shielded overall with a shielding material such as aluminium.

Figure 3:
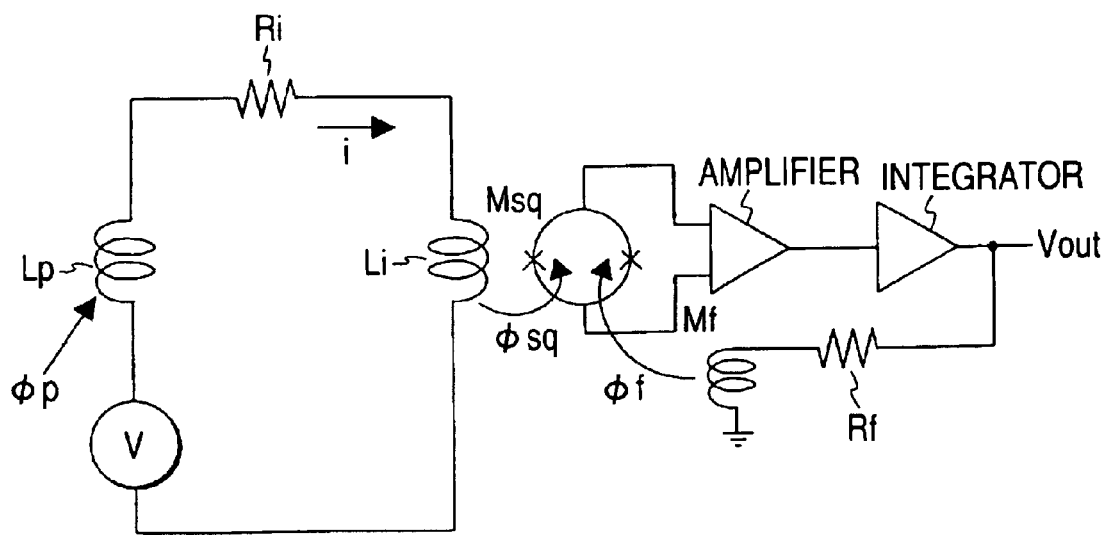
FIG. 3 is a diagram of an equivalent circuit in the apparatus of the first embodiment.

FIG. 3 is a schematic diagram of an equivalent circuit when the pickup coil is made of the normal conducting member in the present embodiment. A voltage induced by the normal conducting coil is defined as $j\omega\Phi p$ (Equation (3)). The relationship between a flux $\Phi p$ fed to the pickup coil and a flux $\Phi sq$ transferred to the SQUID ring is calculated according to the following equations:

$$V=(Ri+j\omega(Lp+Li))*i \quad (1)$$

$$\Phi sq=Msq*i \quad (2)$$

$$V=d\Phi p/dt=j\omega\Phi p \quad (3)$$

wherein V is the voltage induced in the pickup coil; Ri is the resistance (9 Ω) between the pickup coil and the input coil; Lp is the inductance of the pickup coil (0.7 mH); Li is the inductance of the input coil (250 nH); i is the current passing through the loop of the input coil and the pickup coil; ω is the angular frequency; and Msq is the self-inductance of the SQUID. In an actual apparatus, a dumping resistance (22 Ω) and a capacitor (0.47 µF) are connected in parallel with the input coil, but these components do not significantly affect the calculation and are not shown in the figures and equations.

From the equations (1), (2) and (3), the relationship between $\Phi sq$ and $\Phi p$ can be expressed by the following equation:

$$\Phi sq=Msq/\Phi p=Msq/(R/(j\omega)+(Lp+Li)) \quad (4)$$

The relationship between $\Phi sq$ and the output Vout of the FLL circuit can be expressed by the following equations:

$$\Phi f=Mf*Vout/Rf \quad (5)$$

$$\Phi p=Bp*S \quad (6)$$

wherein Bp is the flux density detected by the pickup coil; and S is the area of the pickup coil. The relationship between the magnetic field input into the pickup coil and the output voltage of the FLL circuit can be expressed by the following equation (7) provided that $\Phi sq$ is identical to $\Phi f$:

$$Bp/Vout=Rf*S/Mf*Msq/(R/(j\omega)+(Lp+Li)) \quad (7)$$

The equation (7) yields the ratio of the external magnetic field applied to the pickup coil to the voltage induced in the pickup coil, i.e., 1 V can be inverted into a magnetic field of how many teslas. In other words, the ratio corresponds to the reciprocal of how many voltages of the voltage an external magnetic field of 1 tesla can induce in the pickup coil and corresponds to the sensitivity of the magnetometer. The equation (7) shows that the sensitivity of the magnetometer decreases with an increasing frequency and that the magnetometer-can detect a weaker magnetic field in a higher frequency. The cutoff frequency fc1 in the equation (7) can be expressed by the following equation:

$$fc1=R/(2\pi(Lp+Li)) \quad (8)$$

The cutoff frequency fc1 in the present embodiment is 2.0 kHz.

Next, the flux noise generated from the resistance Ri of the pickup coil is calculated. The voltage noise Vn generated by the resistance Ri is expressed by the equation: $Vn=\sqrt{(4*k*T*Ri)}$ wherein k is the Boltzmann constant ($1.37\times10^{-23}$); and T is the temperature. Vn in the present embodiment is $3.6\times10^{-10}$ V/√Hz provided that T is 300 K and Ri is 9 Ω. The flux noise Φn detected by the SQUID ring is expressed by the following equation:

$$\Phi n = Msq * Vn/(R+j\omega(Lp+Li)) \quad (9)$$

When ω is sufficiently low (ω=0), Φsq is $1.3 \times 10^{-4}$ $\ddot{O}_0$/√Hz. The value Φsq satisfactorily coincides with a flux noise level of 1 kHz or less in FIG. 5. The cutoff frequency fc2 in the equation (9) can be expressed by the following equation:

$$fc2 = (R/(2\pi(Lp+Li))) \quad (10)$$

The cutoff frequency fc2 in the present embodiment is 2 kHz. Accordingly, the cutoff frequency fc1 is identical to the cutoff frequency fc2.

Figure 4:
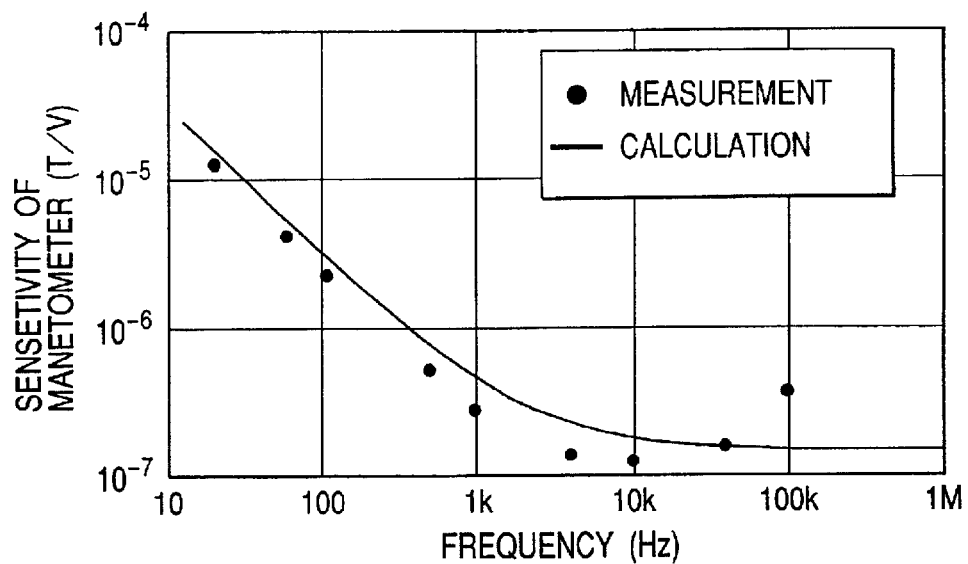
FIG. 4 is a graph showing the relationship between the frequency and the magnetometer sensitivity in the apparatus of the first embodiment as actual measurements and calculations.

FIG. 4 shows the relationship between the sensitivity of the magnetometer and the frequency as actual measurements and calculation results according to the equation (7). The actual measurements are found to be in good agreement with the calculation results, indicating that the sensitivity increases with an increasing frequency. The sensitivity as the actual measurements decreases at frequencies of 50 kHz or more as compared with the calculation results. This is because the dumping capacitor (0.47 μF) connected in parallel with the input coil serves as a low-pass filter with the cutoff frequency $fc2 = 1/(2\pi RiC) = 38$ kHz.

Figure 5:
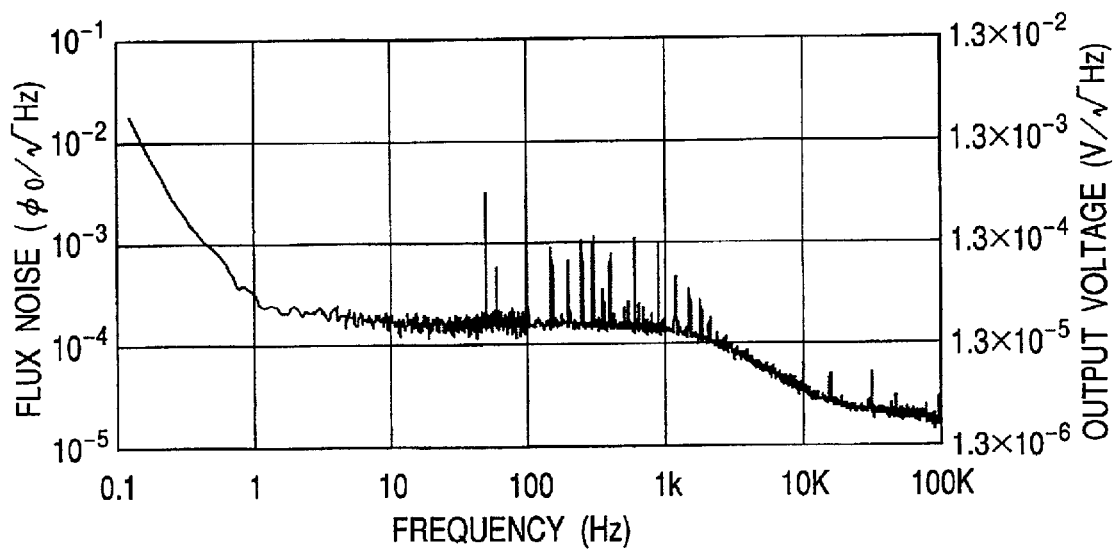
FIG. 5 is a graph showing the relationship as actual measurements between the flux noise and the frequency in the apparatus of the first embodiment.

FIG. 5 shows actual measurements of the flux noise. In FIG. 5, values obtained by converting the flux noise to an output voltage are plotted on the right ordinate. FIG. 5 shows that the noise level is as high as Ri noise of $1.3 \times 10^{-4}$ $\Phi_0$/√Hz at frequencies of 1 kHz or less as calculated according to the equation (9), and that the cutoff frequency as calculated according to the equation (10) substantially coincides with the actual measurement.

The magnetic field resolution of the overall magnetometer can be calculated by multiplying the sensitivity shown in FIG. 4 by the output voltage shown in FIG. 5. The magnetic field resolution is, for example, 90 fT/√Hz at 10 kHz. The magnetic field resolution attains the minimum at a frequency of about 10 kHz.

FIG. 6 shows impedance magnetocardiogram waveforms as measured at two positions on the thoracic wall of a healthy male subject (34 years old). A current of 7 mA peak-to-peak was fed during measurement. To avoid the influence of breathing, the waveforms were measured during non-breathing for 15 seconds after inhalation. An impedance magnetocardiogram waveform which is considered as significantly clearly corresponds to the heartbeat was observed at the position 1 near to the heart. A raw waveform of the impedance magnetocardiogram was observed at the position 2, although it was somewhat weak.

To analyze these waveforms in more detail, each of the peaks of the impedance waveforms was subjected to 10-times averaging, and results are shown in FIGS. 7(a) and 7(b) indicating that clearer and sharper waveforms can be obtained by averaging. As thus described, the apparatus according to the present embodiment includes a monitor that can display plural averaged waveforms or raw waveforms.

Figure 16:
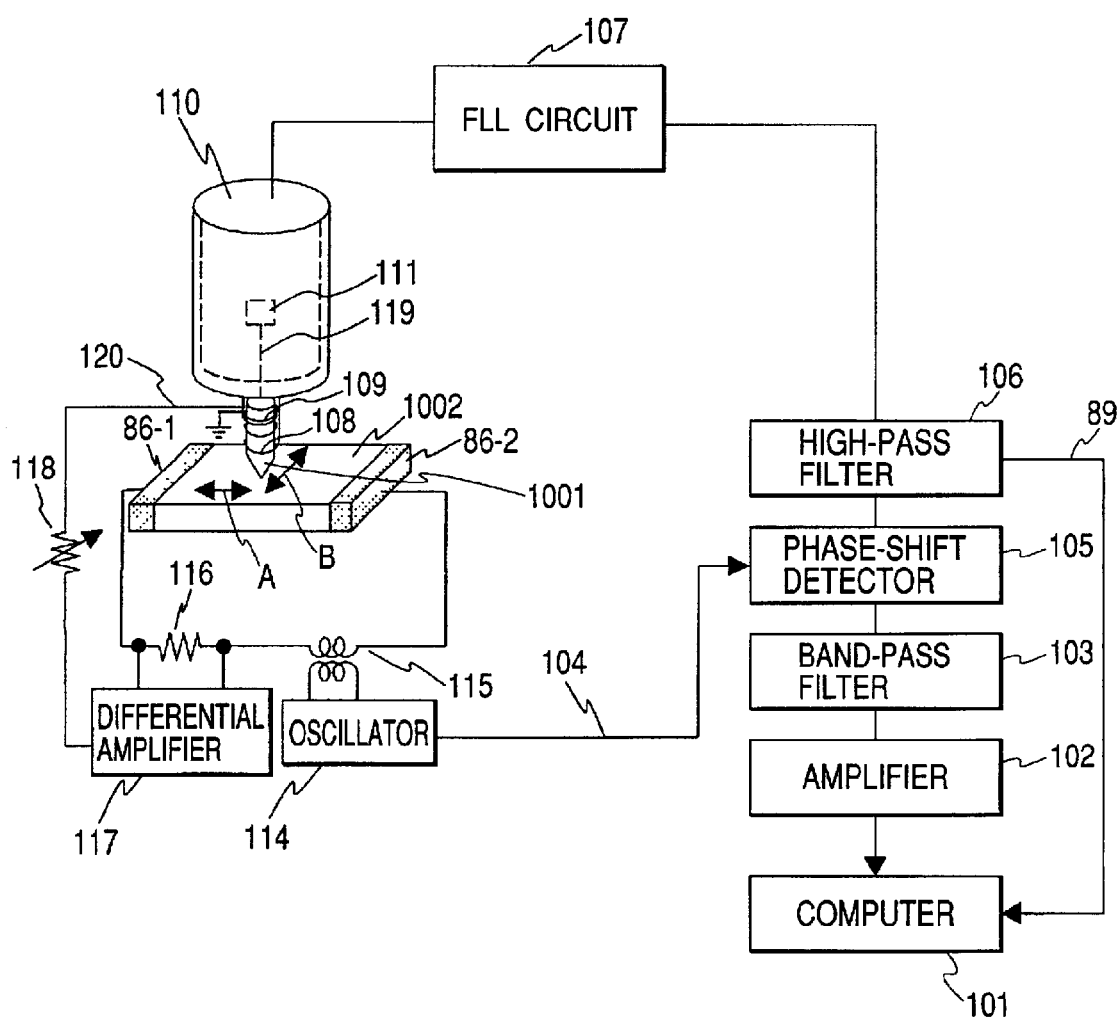
FIG. 16 is a schematic diagram illustrating, in detail, an apparatus for measuring a magnetic field using the high-temperature superconducting SQUID of FIG. 15 as the ninth embodiment of the present invention; and, FIG. 17 is a schematic diagram of an apparatus for measuring a magnetic field as a tenth embodiment of the present invention.

In the apparatus according to First Embodiment as illustrated above, the pickup coil part 108 is arranged independently outside the cryostat 110. However, it is also acceptable that the pickup coil part is affixed to the outer layer of the cryostat 110, and the lead line part 119 is allowed to penetrate the vacuum part of the cryostat and is electrically or magnetically connected to the SQUID 111 (FIG. 16). By this configuration, the lead line part 119 can be shortened to thereby avoid deterioration in flux transferring to the SQUID 111 due to the inductance of the lead line part 119. In addition, the electromagnetic interference in the lead line part induced by the high frequency electromagnetic waves can be reduced.

Second Embodiment

Figure 8:
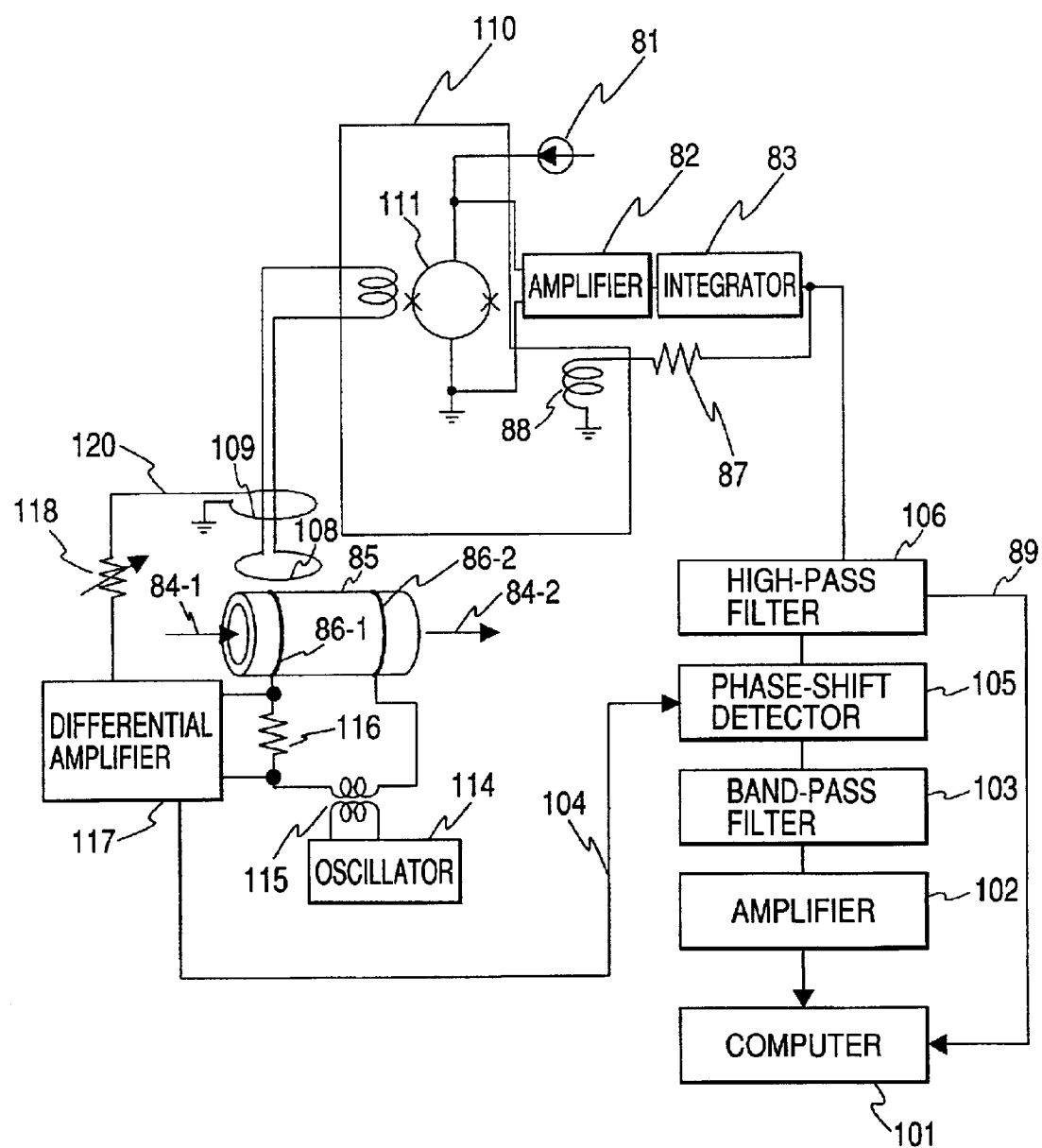
FIG. 8 is a schematic diagram of an apparatus for measuring a magnetic field as a second embodiment of the present invention.

The second embodiment of the present invention will be illustrated with reference to FIG. 8. A cylinder 85 is hollow inside thereof to pass a highly conductive member such as water from an inlet 84-1 to an outlet 84-2. In the present embodiment, the cylinder 85 is made of a highly conductive member such as copper, and a high frequency current is fed from electrodes 86-1 and 86-2 through the cylinder 85. Specifically, a high frequency voltage generated by the oscillator 114 is transferred via the transformer 115 and is applied from the electrodes 86-1 and 86-2 via the resistance 116. The applied high frequency current flow through both the conductor constituting the cylinder 85 and the water fed into the cylinder 85. When the fed water is contaminated with impurities or other foreign matters, the pickup coil 108 can detect changes in current due to the impurities. The compensation coil with an inverse phase 109 for generating a magnetic field with an inverse phase is arranged in the vicinity of the pickup coil 108.

Since the compensation coil with an inverse phase 109 detects an actual current flowing through the conductor as in First Embodiment, the voltage between the both ends of the resistance 116 is amplified by the differential amplifier 117. Based on the output of the differential amplifier 117, the variable resistance 118 controls the amount of the current to be fed to the compensation coil with an inverse phase 109. By action of the compensation magnetic field with an inverse phase generated by the compensation coil with an inverse phase 109, a change in current alone can be detected with a high sensitivity. The change detected by the pickup coil 108 is transmitted to the SQUID 111 arranged in the cryostat 110 to thereby be converted into a voltage. The cryostat 110 houses a cooling medium.

The inner configuration of the FLL circuit 107 shown in FIG. 1 will be illustrated with reference to FIG. 8. The FLL circuit 107 includes a current bias 81 for applying a bias current, an amplifier 82, an integrator 83 and a feedback resistance 87 to operate the SQUID 111 as a magnetometer. A feedback coil 88 is housed in the SQUID 111. The feedback resistance 87 and the feedback coil 88 constitute a feedback circuit that can convert magnetic fields into voltages as linear functions.

The output of the FLL circuit is transferred to the high-pass filter 106 and is detected by the phase-shift detector 105 using the reference signal 104 as the frequency of the current flowing therethrough. The output of the phase-shift detector 105 is transferred to the band-pass filter 103, is then amplified by the amplifier 102, and is stored in the computer 101 as digital data. The computer 101 displays or analyses the digital data as waveforms.

An output 89 of the band-pass filter 103 is used in measurement of the absolute value of the impedance. The absolute value of the impedance can be determined by measuring the impedance without the application of the compensation magnetic field with an inverse phase generated by the compensation coil with an inverse phase 109. Alternatively, it can be calculated from the absolute values of the current flowing through the conductor obtained from the output of the differential amplifier 117 and the frequency of the applied magnetic field, when a compensation magnetic field with an inverse phase in a known amount is applied. Consequently, to measure the absolute value of the impedance, it is also acceptable that the apparatus further comprises a controller for the compensation magnetic field with an inverse phase, and the variable resistance 118 has a control mechanism for automatic determination of the amount of the compensation magnetic field by action of the controller, while these components are not shown in the figure. The control mechanism can automatically determine the amount of the compensation magnetic field, for example, by automatically detecting the absolute value or maximum of the high frequency magnetic field obtained from the output 89 by the computer 101 and controlling the variable resistance 118 so as to minimize the resulting high frequency magnetic field. The apparatus according to First Embodiment shown in FIG. 1 can also comprise such a control mechanism for automatic determination of the amount of the compensation magnetic field.

In Second Embodiment, the apparatus is illustrated by taking a conductor cylinder 85 as an example. However, it is also acceptable that the cylinder 85 is made of a nonconducting material and the electrodes 86-1 and 86-2 are arranged inside the cylinder 85.

The apparatus for measuring a magnetic field according to the present embodiment can highly accurately detect changes in water quality flowing through the cylinder and can be used, for example, as an apparatus for monitoring the quality of water and other fluids flowing through piping.

Third Embodiment

Figure 9:
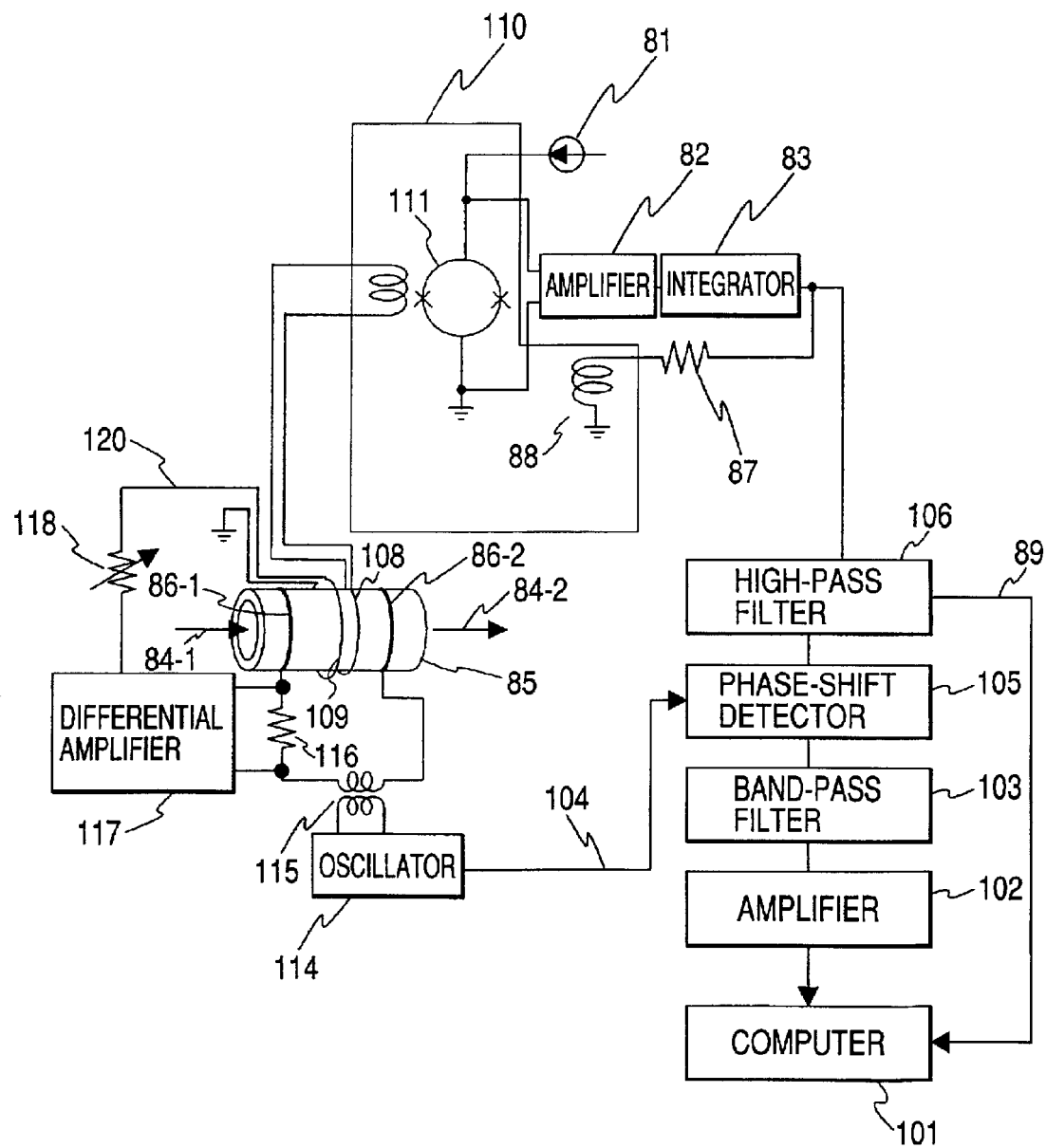
FIG. 9 is a schematic diagram of an apparatus for measuring a magnetic field as a third embodiment of the present invention.

The third embodiment of the present invention will be illustrated with reference to FIG. 9. The FLL circuit, detecting process and circuitry of the apparatus are the same as in Second Embodiment shown in FIG. 8, and explanations thereof are omitted. In contrast to the apparatus of Second Embodiment shown in FIG. 8, the apparatus shown in FIG. 9 has a feature in that the detection direction of the pickup coil 108 is perpendicular to the direction of the high frequency current flowing therethrough. According to this configuration, the pickup coil 108 does not require cooling in, for example, a cryostat, and the inspected subject can be placed in the pickup coil at ordinary temperature.

Fourth Embodiment

Figure 10:
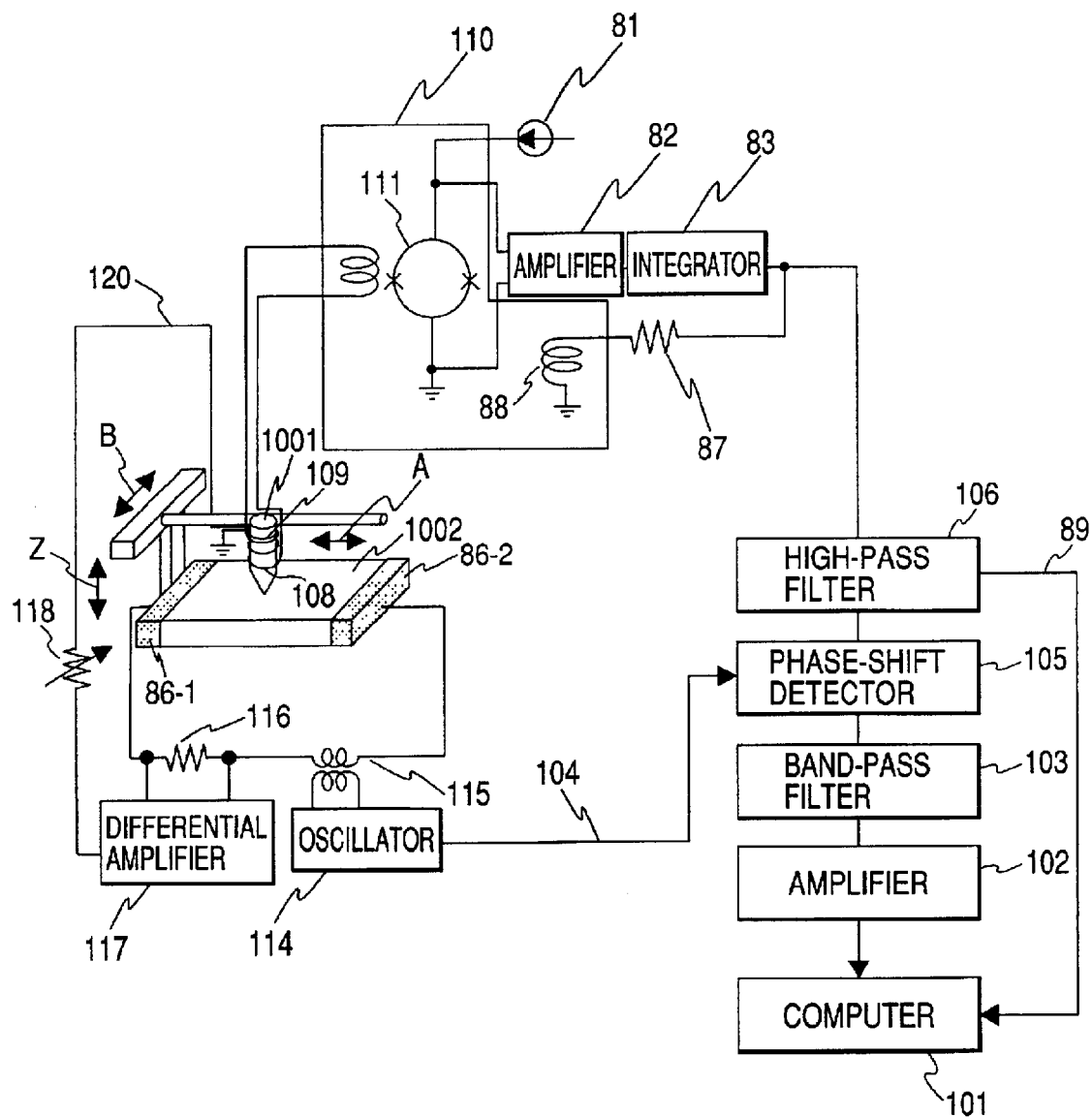
FIG. 10 is a schematic diagram of an apparatus for measuring a magnetic field as a fourth embodiment of the present invention.

The fourth embodiment of the present invention will be illustrated with reference to FIG. 10. The FLL circuit, detecting process and circuitry of the apparatus are the same as in Second Embodiment shown in FIG. 8, and explanations thereof are omitted. According to the present embodiment, a detecting probe 1001 around which the pickup coil 108 is placed is used to thereby measure a magnetic field with a high spatial resolution. When the detecting probe is made of a soft-magnetic material having a high permeability, such as Permalloy (trade name), the resulting detecting probe has an increased sensitivity to the magnetic field. By sharpening the tip of the probe to a width of about several tens micrometers, the resulting probe can have a further increased sensitivity.

A movement apparatus of relative position 1003 for holding the probe and changing a relative position of the probe to the inspected subject is mounted on the detecting probe 1001 to thereby enable the detecting probe 1001 to scan in the directions A and B perpendicular to each other and in the height direction Z. A stepping motor or an actuator is used for scanning. The use of a piezoelectric element such as a piezoelectric actuator enables minute or fine movement on the order of about several micrometers. As an inspected subject 1002, copper, aluminium or another conductor that can pass an alternating current therethrough is used. The apparatus herein detects a magnetic field corresponding to a change in bias of a high frequency current flowing steady and can therefore nondestructively inspect a subject, for example, to detect cracks inside a substance with a high sensitivity. To determine a spatial change in magnetic field using the apparatus having a configuration of FIG. 10, the band-pass filter 103 comprises a low-pass filter function alone, and a direct current bias component detected in the plane under measurement is cancelled by the compensation coil with an inverse phase 109. Such an apparatus having this configuration can detect a minute change in magnetic field caused for example by cracks in a conductor with a high sensitivity and can be used for nondestructive inspection.

Fifth Embodiment

Figure 11:
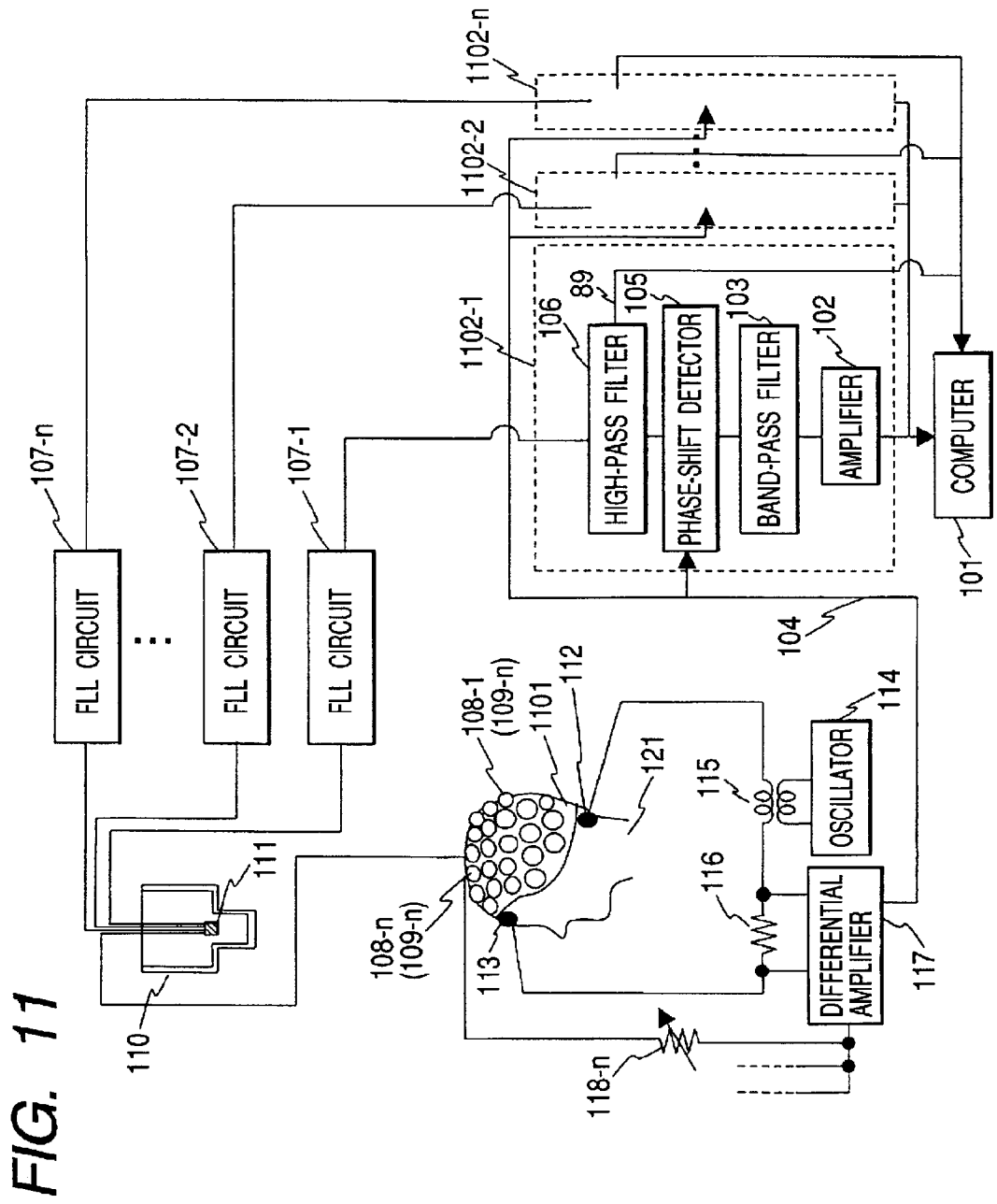
FIG. 11 is a schematic diagram of an apparatus for measuring a magnetic field as a fifth embodiment of the present invention.

The fifth embodiment of the present invention will be illustrated with reference to FIG. 11. The FLL circuit, detecting process and circuitry of the apparatus are the same as in Second Embodiment shown in FIG. 8, and explanations thereof are omitted. The apparatus according to the present embodiment comprises plural units of the configuration shown in FIG. 1. This apparatus includes demodulation circuits 1102. The pickup coils 108 are ordinary-temperature coils, are arranged outside the cryostat 110 and can therefore be arranged in intimate contact with the head of a subject. The apparatus according to the present embodiment includes the pickup coils 108-1 . . . 108-n fixed on a cap 1101 and can thereby detect a magnetic field of the subject only by placing the cap 1101 on the head of the subject. In the apparatus, the accurate positional relationship among the pickup coils can be obtained, and the apparatus enables impedance CT (computed tomography) using a magnetic field.

Sixth Embodiment

Figure 12:
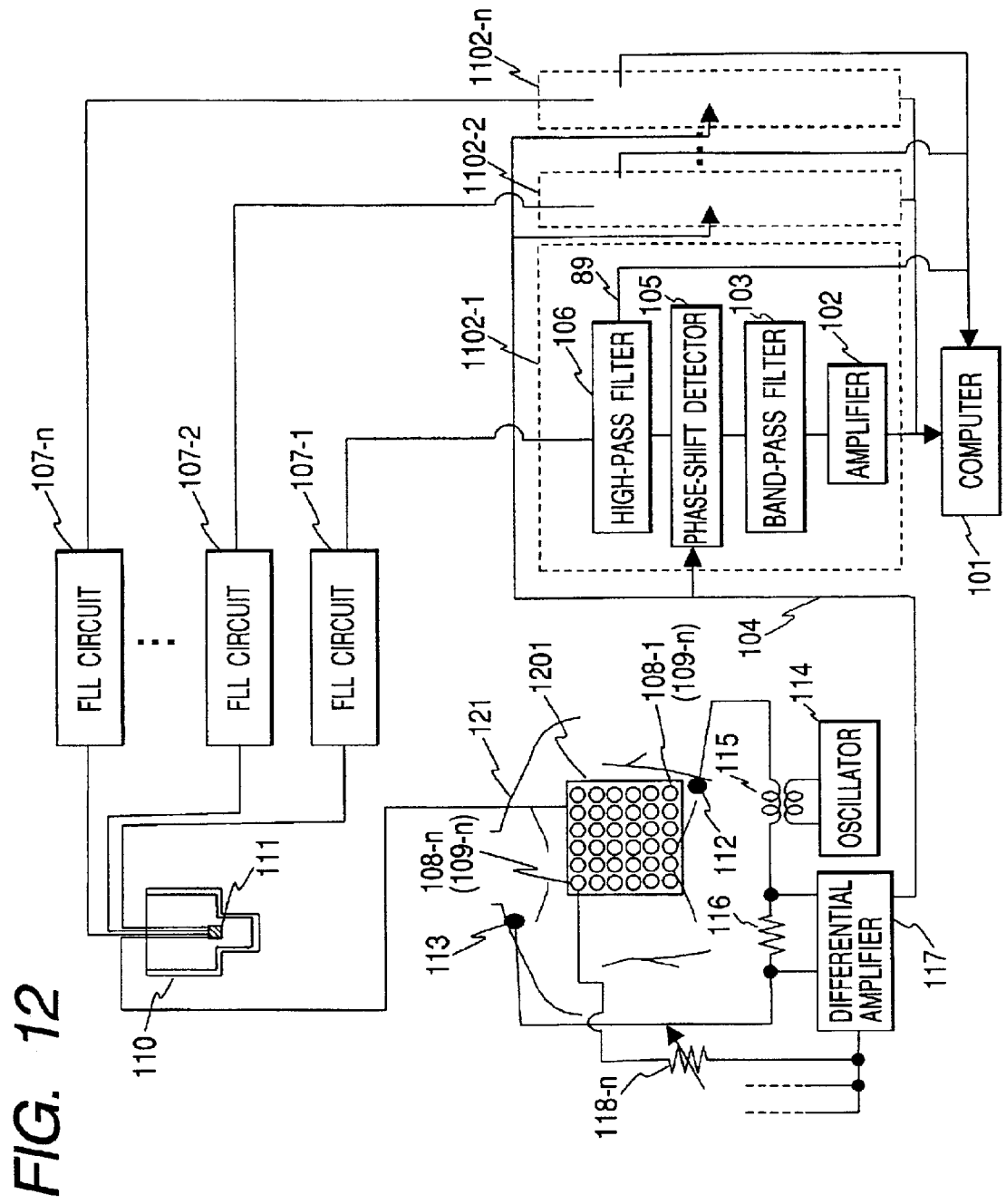
FIG. 12 is a schematic diagram of an apparatus for measuring a magnetic field as a sixth embodiment of the present invention.

The sixth embodiment of the present invention will be illustrated with reference to FIG. 12. The FLL circuit, detecting process and circuitry of the apparatus are the same as in Second Embodiment shown in FIG. 8, and explanations thereof are omitted. The apparatus according to the present embodiment comprises plural units of the configuration shown in FIG. 1. The pickup coils 108 are ordinary-temperature coils, are arranged outside the cryostat 110 and can therefore be arranged in intimate contact with the breast of a subject. An arrangement of the pickup coils 108 on a sheet 1201 enables measurement of two-dimensional impedance magnetocardiograms. The apparatus according to the present embodiment is illustrated by taking pickup coils 108 arranged two-dimensionally as an example. However, with an arrangement of the pickup coils 108 to place the same around once, the body of the subject enables reconstruction of impedance CT (computed tomography) images using a magnetic field.

Seventh Embodiment

Figure 13:
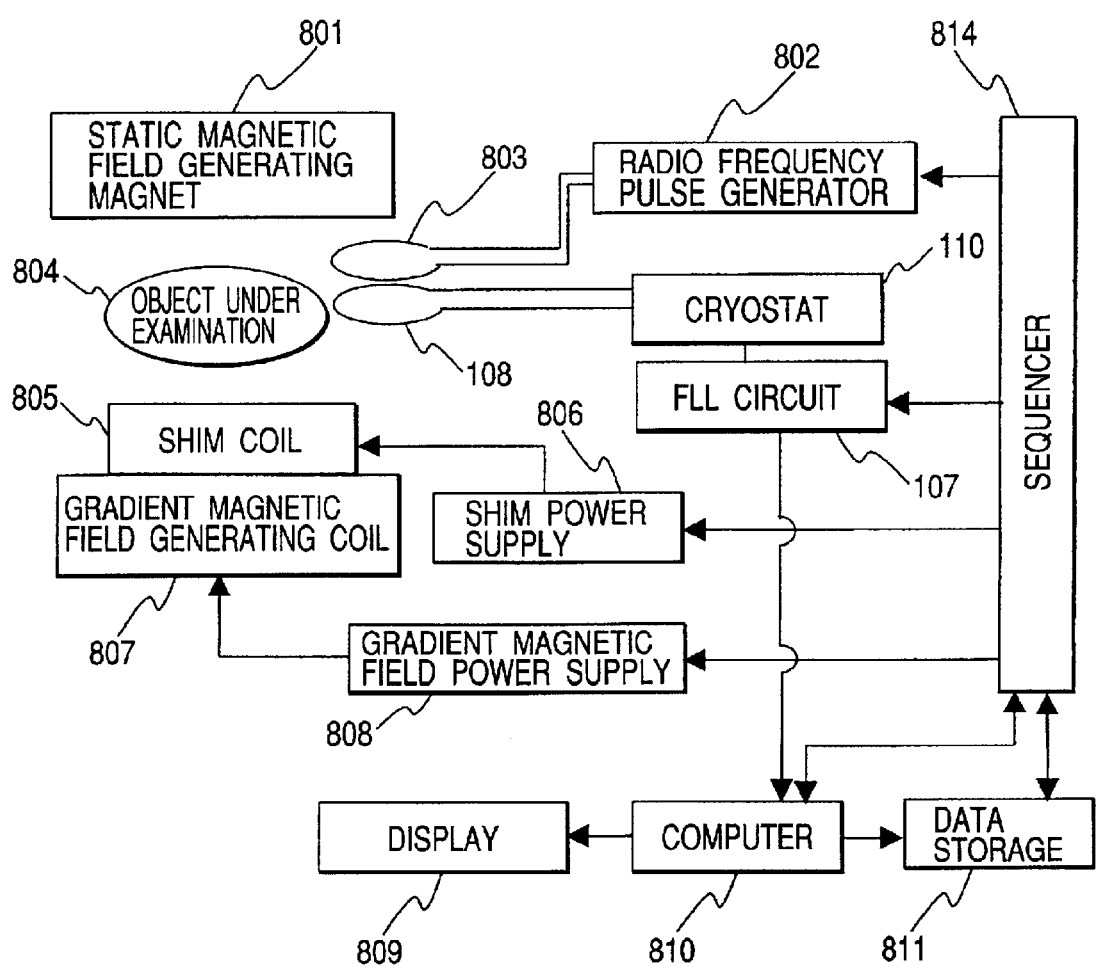
FIG. 13 is a schematic diagram of an apparatus for measuring a magnetic field as a seventh embodiment of the present invention.

The seventh embodiment of the present invention will be illustrated with reference to FIG. 13. In the apparatus according to the present embodiment, the pickup coil 108 arranged outside the cryostat 110 is used to detect nuclear magnetic resonance (NMR) signals. An object under examination 804 is surrounded by a static magnetic field generating magnet 801, a gradient magnetic field generating coil 807 and a high frequency pulse power supply 803, and the pickup coil 108 is brought close to the object under examination 804 to thereby detect the NMR signals. A shim power supply 806 and a gradient magnetic field power supply 808 are connected to a shim coil 805 for cancellation of distortion in static magnetic field, are controlled by a sequencer 814 and detect NMR image signals at individual cross sections. The sequencer 814 controls these components based on a sequence stored in a data storage 811. The NMR signal output from the FLL circuit 107 is recorded on a computer 810, and each NMR image at each cross section is displayed on a display 809. In the apparatus according to the present embodiment, the demodulation circuits and compensation coils used in First through Fourth Embodiments are not used, and the FLL circuit 107 operates the SQUID as a magnetometer, and the ordinary-temperature coil detects the NMR signals. According to conventional techniques, the NMR signals are detected by amplification of a voltage induced in an ordinary-temperature coil, and a resonance frequency increases with an increasing intensity of a magnetic field generated by the static magnetic field generating magnet 801 to increase the induced voltage. However, when the intensity of the static magnetic field generating magnet 801 is weakened, a voltage induced in the ordinary-temperature coil become too low to be detected. According to other conventional techniques, the NMR signals are detected by using the SQUID, but the pickup coil 108 in the conventional techniques is placed inside the cryostat and cannot be brought sufficiently close to the object under examination 804. Thus, sufficient detection signals are not obtained. In contrast, the apparatus according to the present embodiment can detect, with a high sensitivity, such a weak magnetic field once detected by the ordinary-temperature coil by action of the SQUID arranged inside the cryostat 110. In addition, it does not invite a voltage induced by a direct current magnetic field as shown in FIG. 4, and there is no need for consideration of the influence of the direct current magnetic field that causes the SQUID to malfunction. Accordingly, the apparatus does not malfunction even in a static magnetic field and can detect the NMR signals with a high sensitivity.

Eighth Embodiment

Figure 14:
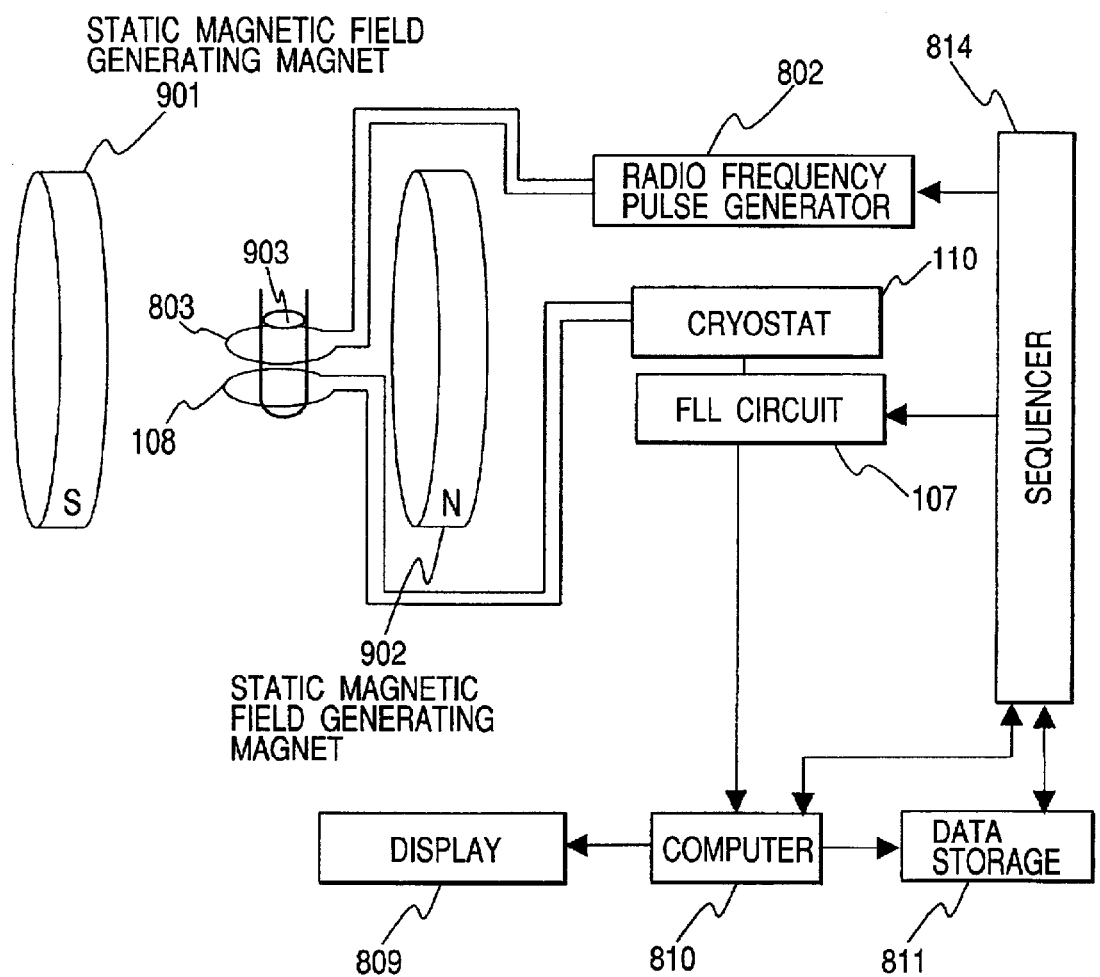
FIG. 14 is a schematic diagram of an apparatus for measuring a magnetic field as an eighth embodiment of the present invention.

The eighth embodiment of the present invention will be illustrated with reference to FIG. 14. In the present embodiment, the invention is applied to a nuclear magnetic resonance apparatus for use in structural analysis of proteins as a result of gene expression. The pickup coil 108 is placed around a sample holder 903 sandwiched between static magnetic field generating magnets 901 and 902 and detects the NMR signals. The components other than this are similar to those in the apparatus according to Seventh Embodiment shown in FIG. 13 and explanations thereof are omitted. The pickup coil for use in the invention can be placed around the sample holder 903 at ordinary temperature as in this apparatus and can detect a magnetic field with a high sensitivity.

Ninth Embodiment

Figure 15:
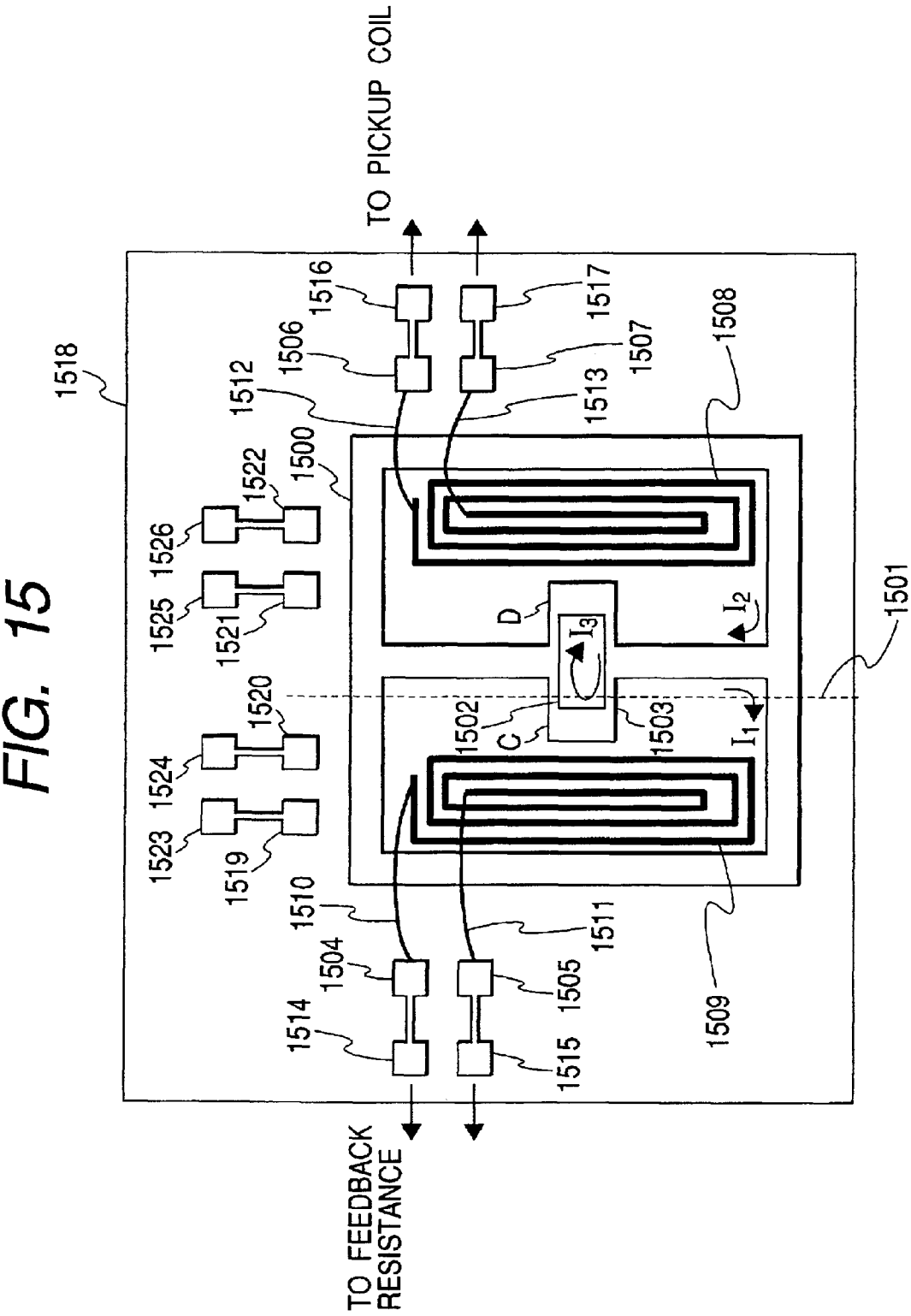
FIG. 15 is a schematic diagram of a high-temperature superconducting SQUID in a ninth embodiment of the present invention.

FIG. 15 shows a device structure of a high-temperature superconducting SQUID as the ninth embodiment of the present invention. A pattern 1500 in the form of the symbol infinity ($\infty$) is made of a high-temperature superconducting member on a print circuit board 1518. By forming the pattern 1500 in the form of the symbol infinity ($\infty$), induced currents I1 and I2 are generated in the right and left portions of the pattern, respectively, by action of a flux fed to the pattern 1500, and the difference between the induced currents I1 and I2 flows as a current I3 through a ring including Josephson junctions 1502 and 1503. The high-temperature superconducting SQUID detects a flux by action of the current I3 and converts the same into a voltage. By forming the pattern in the form of the symbol infinity ($\infty$), the resulting device becomes resistant to external flux noise.

The device includes a feedback coil part 1509 in one of the right and left portions of the pattern 1500 in the form of the symbol infinity ($\infty$) and an input coil part 1508 in the other. In addition, the print circuit board 1518 includes line connection pads 1514, 1515, 1516, and 1517. A pad 1504 is wired patternwise with the line connection pad 1514 and is electrically connected to one end of the feedback coil part 1509 via a bonding part 1510. The pad 1504, line connection pad 1514 and bonding 1510 may be connected with one another by bonding with a metal material such as aluminium. Likewise, a pad 1505 is wired patternwise with the line connection pad 1515 and is electrically connected to the other end of the feedback coil part 1509 by bonding 1511. The feedback coil part 1509 corresponds to the feedback coil 88 shown in FIG. 8, and the line connection pads 1514 and 1515 are electrically connected to the feedback resistance 87 arranged outside the cryostat 110. On the pickup coil side, pads 1506 and 1507 are wired patternwise with the line connection pads 1516 and 1517, respectively, and are electrically connected to the input coil part 1508 via bondings 1512 and 1513. The input coil part 1508 corresponds to an input coil which transfers a flux from the pickup coil 108 to the SQUID 111 shown in FIG. 8. The input coil part 1508 is electrically connected to an ordinary-temperature pickup coil arranged outside the cryostat. The print circuit board 1518 further comprises pads 1519, 1520, 1521, and 1522 and line connection pads 1523, 1524, 1525, and 1526 that are bonded to bonding parts C and D to thereby detect an input current bias and an output voltage. In this connection, FIG. 15 also shows a bicrystal line 1501. As thus described, by forming the pattern 1500 in the form of the symbol infinity ($\infty$), the resulting device becomes resistant to external noise magnetic fields. In addition, by forming the input coil in one of the right and left portions of the pattern and the feedback coil in the other, the high-temperature superconducting SQUID can detect a magnetic field with a high sensitivity.

FIG. 16 shows a configuration of an apparatus for measuring a magnetic field using the high-temperature superconducting SQUID shown in FIG. 15. However, such an apparatus can also be formed by using a niobium SQUID. The apparatus according to the present embodiment corresponds to a detailed configuration of the cryostat in Fourth Embodiment shown in FIG. 10. In the apparatus according to Ninth Embodiment, the SQUID 111 is arranged inside the cryostat 110, and the lead line part 119 from the SQUID 111 penetrates the vacuum layer at the bottom of the cryostat 110 and is electrically connected to the pickup coil 108. The detecting probe 1001 is fixed at the bottom of the cryostat 110. By fixing the detecting probe 1001 with the cryostat 110, the resulting apparatus can easily be handled.

The scanning operation of the apparatus according to the present embodiment will be illustrated below. Specifically, to map, within the inspected subject 1002, the current value of a high frequency current flowing through the inspected subject 1002, the band-pass filter 103 used in the apparatus comprises a low-pass filter alone without high-pass filter. To yield the same effect as in a high-pass filter, the compensation coil with an inverse phase 109 is used to cancel direct current components in the output of the phase-shift detector 105. By scanning in the directions A and B using the apparatus having the aforementioned configuration, the flowing current in the plane of the inspected subject 1002 can be mapped.

Tenth Embodiment

Figure 17:
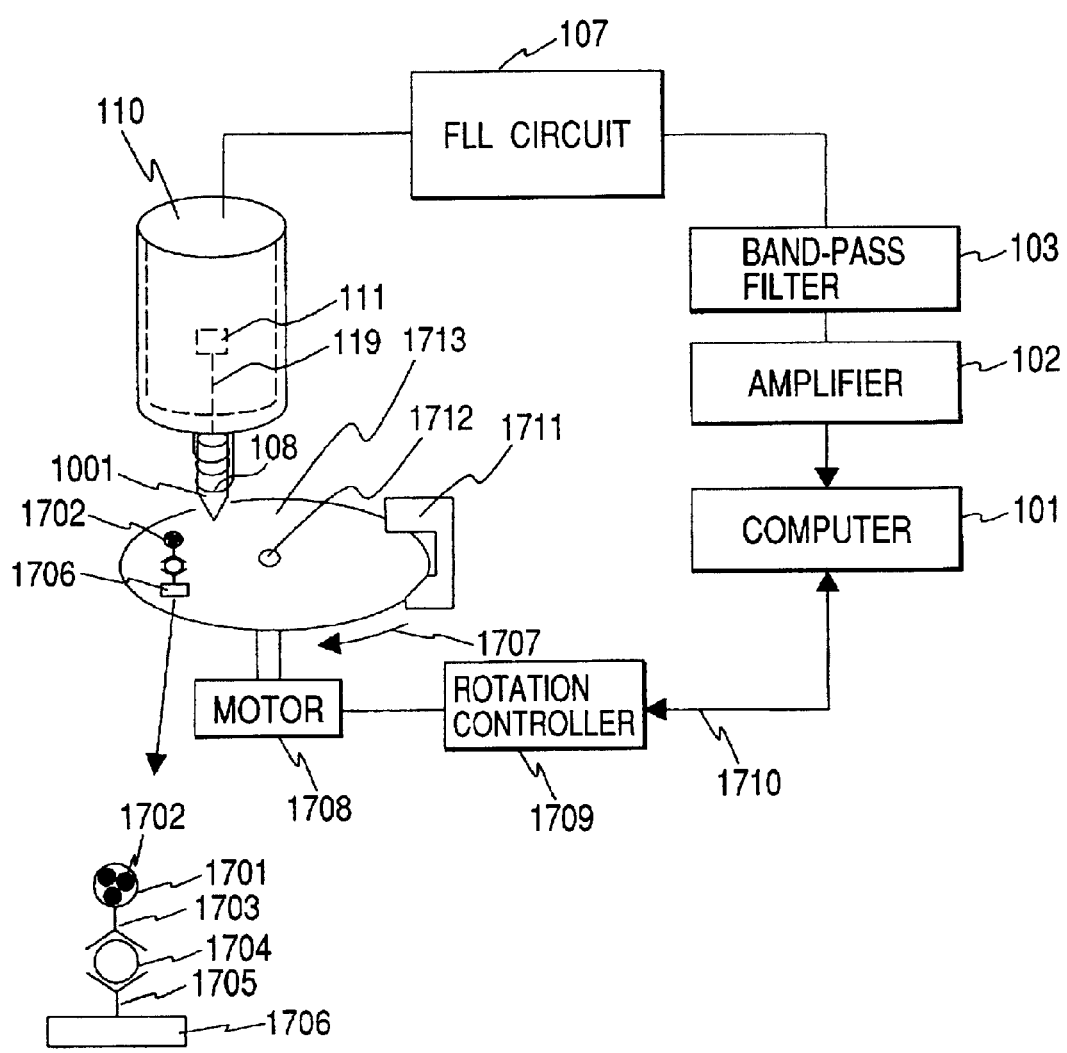

FIG. 17 illustrates in detail an apparatus according to the tenth embodiment of the present invention. A sample is labeled with a magnetic marker as a result of antigen-antibody immunoreaction and is placed on a rotator 1713. The sample is marked in the following manner. Specifically, as shown at the bottom of FIG. 17, an antibody for holding 1705 is fixed on a substrate 1706 and is allowed to react with an antigen 1704, and an antibody for detection 1703 labeled with a polymer 1701 including a magnetic particle 1702 as a marker is allowed to react with the antigen 1704 to thereby constitute the labeled sample. The apparatus also comprises a magnet 1711 for magnetizing the magnetic particle 1702 upon rotation of the sample on the rotator 1713. The sample with the marker magnetic particle 1702 passes in the vicinity of the magnet 1711 on every rotation, and the magnetic field can be detected with a high sensitivity. A rotation controller 1709 controls the rotation of the rotator 1713 by controlling a motor 1708 to rotate with an axis of a rotation axis 1712 under a command of the computer 101. The rotation controller 1709 outputs a trigger signal upon every rotation, and the trigger signal is input into the computer 101 for averaging. The speed of rotation is preferably set at such a speed corresponding to the frequency to be measured, such as 10 kHz. When the frequency to be measured is 10 kHz, the rotation speed is preferably equal to or more than 10000 per second (600000 rpm). However, it is difficult in actuality to rotate the rotator at such a high speed, and the S/N ratio is improved by increasing the number of averaging. According to the apparatus of the present embodiment, the pickup coil 108 is arranged outside the cryostat 110, can thereby be brought close to the inspected subject and can detect a magnetic field with a higher sensitivity. The aforementioned configuration of the present embodiment can also be applied to conventional apparatus in which the pickup coil is arranged inside the cryostat.

While the present invention has been described with reference to what are presently considered to be the preferred embodiments, it is to be understood that the invention is not limited to the disclosed embodiments. On the contrary, the invention is intended to cover various modifications and equivalent arrangements included within the sprit and scope of the appended claims. The scope of the following claims is to be accorded the broadest interpretation so as to encompass all such modifications and equivalent structures and functions.

While not clearly shown in the appended claims, the invention also relates to the following modifications.

(1) Specifically, the present invention relates to a magnetic resonance apparatus. The apparatus comprises a static magnetic field generating magnet, a gradient magnetic field generating means, an alternating magnetic field generating means, a subject- or sample-holder arranged between the static magnetic field generating magnet and the gradient magnetic field generating means, a pickup coil for detecting a magnetic resonance signal induced in the subject or sample held by the holder, a superconducting quantum interference device connected to the pickup coil, a cryostat for holding the superconducting quantum interference device, a computer for processing the nuclear magnetic resonance signal and reconstructing an image, and a display for displaying the reconstructed image. In the apparatus, the pickup coil comprises a normal-conducting member and is arranged outside the cryostat.

(2) In the magnetic resonance apparatus, the holder is preferably a sample holder around which the pickup coil is placed.

(3) The invention also relates to an apparatus for measuring a magnetic field comprising a sample including a magnetic particle, a means for applying an external magnetic field to the sample, a rotator for holding the sample, a driving means for rotating the rotator, a pickup coil for detecting a magnetic field generated in the sample, a superconducting quantum interference device connected to the pickup coil, and a cryostat for holding the superconducting quantum interference device at low temperatures. In the apparatus, the pickup coil comprises a normal-conducting member and is arranged outside the cryostat.

(4) The apparatus mentioned in the above (3) for measuring a magnetic field preferably further comprises a controller for controlling the rotation of the driving means.

(5) The apparatus mentioned in the above (3) preferably further comprises a means for averaging magnetic field waveforms detected by the pickup coil.

As is described above, the apparatus of the present invention can detect magnetic field change signals or nuclear magnetic resonance signals obtained by passing a high frequency current through a living body, by the use of the pickup coil that is placed at ordinary temperature and is magnetically or electrically connected to the SQUID.

What is claimed is:

1. An apparatus for measuring a magnetic field, comprising:

an oscillator which generates an alternating voltage;

a transformer which transfers said alternating voltage to an alternating current;

two electrodes which are placed in two positions of a living body, said alternating current being fed to said living body via said two electrodes;

a superconducting quantum interference device which is arranged in a cryostat;

a pickup coil which detects a magnetic field induced in said living body by feeding said alternating current therethrough, said pickup coil being connected to said superconducting quantum interference device electrically or magnetically, made of a normal conducting material and arranged outside said cryostat;

a differential amplifier which amplifies a potential between both ends of a resistance arranged in a line connecting said two electrodes in order to monitor a frequency of said alternating current fed to said living body;

a compensation coil which produces a compensation magnetic field with an inverse phase by feeding an alternating current with an inverse phase with respect to said alternating current fed to said living body, said compensation coil being made of a normal conducting material, arranged outside said cryostat and arranged in the vicinity of said pickup coil such that a magnetic flux is transferred to said pick up coil;

a control device which controls the amount of the alternating current fed to said compensation coil based on current data obtained from said differential amplifier;

a driving circuit which drives said superconducting quantum interference device as a magnetometer and is arranged outside said cryostat;

a high-pass filter circuit to which an output of said driving circuit is fed in order to remove a low frequency noise from said output of said driving circuit;

a phase-shift detector to which an output of said high-pass filter circuit and an output of said differential amplifier are fed in order to detect a phase shift using the frequency of said alternating current fed to said living body as a reference signal;

a band-pass filter circuit to which an output of said phase-shift detector is fed;

an amplifier which amplifies an output of said band-pass filter; and a computer which collects an output of said amplifier and displays said output of said amplifier.

2. The apparatus for measuring a magnetic field according to claim 1, wherein the pickup coil and the compensation coil are placed around a bobbin.

3. The apparatus for measuring a magnetic field according to claim 2, wherein the pickup coil is connected to said superconducting quantum interference device via a first lead line, and the compensation coil is connected to the control device via a second lead line.

4. The apparatus for measuring a magnetic field according to claim 3, wherein the first and second lead lines are twisted.

5. The apparatus for measuring a magnetic field according to claim 3, wherein the first and second lead lines are shielded against external electromagnetic waves.

6. The apparatus for measuring a magnetic field according to claim 3, wherein the first and second lead lines are shielded by a shielding wire which is grounded.

7. The apparatus for measuring a magnetic field according to claim 6, wherein the shielding wire is made of aluminum.

* * * * *